US012751636B2

(12) United States Patent
Doi et al.

(10) Patent No.: US 12,751,636 B2
(45) Date of Patent: Oct. 6, 2026

(54) BLOOD PRESSURE CUFF

(71) Applicant: OMRON HEALTHCARE Co., Ltd., Kyoto (JP)

(72) Inventors: Ryosuke Doi, Kyoto (JP); Minoru Taniguchi, Kyoto (JP); Takayuki Matsuoka, Kyoto (JP); Takayuki Shiina, Kyoto (JP); Yo Imai, Kyoto (JP); Kenji Ozawa, Kyoto (JP); Chisato Tawara, Kyoto (JP)

(73) Assignee: OMRON HEALTHCARE CO., LTD., Kyoto (JP)

( * ) Notice: Subject to any disclaimer, the term of this patent is extended or adjusted under 35 U.S.C. 154(b) by 661 days.

(21) Appl. No.: 18/157,505

(22) Filed: Jan. 20, 2023

(65) Prior Publication Data

US 2023/0148882 A1 May 18, 2023

Related U.S. Application Data

(63) Continuation of application No. PCT/JP2021/025667, filed on Jul. 7, 2021.

(30) Foreign Application Priority Data

Jul. 27, 2020 (JP) ................................ 2020-126733
Feb. 26, 2021 (JP) ................................ 2021-030092

(51) Int. Cl.
*A61B 5/022* (2006.01)

(52) U.S. Cl.
CPC .................................. *A61B 5/022* (2013.01)

(58) Field of Classification Search
None
See application file for complete search history.

(56) References Cited

U.S. PATENT DOCUMENTS 4,838,276 A * 6/1989 Nagai ................ A61B 5/02233 600/499
2009/0234381 A1 9/2009 Karo
(Continued)

FOREIGN PATENT DOCUMENTS

CN 101346100 A 1/2009
CN 205597910 U 9/2016
(Continued)

OTHER PUBLICATIONS

International Search Report (ISR) and its citations, issued for International Application No. PCT/JP2021/025667, Dated Sep. 14, 2021.

(Continued)

*Primary Examiner* — Aurelie H Tu
(74) *Attorney, Agent, or Firm* — Colson Law Group, PLLC

(57) ABSTRACT

Provided is a convenient blood pressure cuff. A blood pressure cuff includes a band-like body enveloping an air bag between an outer cloth and an inner cloth facing the outer cloth; a ring-like member held at a position near one end edge it in a longitudinal direction of the band-like body and extending in a lateral direction of the band-like body; and an auxiliary member stored inside a terminal region between the end edge it of the band-like body and the ring-like member and extending in the lateral direction. The outer cloth and the inner cloth in the terminal region are welded to each other in a state where the auxiliary member is sandwiched between the outer cloth and the inner cloth.

4 Claims, 14 Drawing Sheets

(56) References Cited

U.S. PATENT DOCUMENTS

| | | | | |
|---|---|---|---|---|
| 2010/0268100 A1* | 10/2010 | Nakanishi | .......... | A61B 5/02233 600/499 |
| 2016/0029910 A1 | 2/2016 | Taniguchi et al. | | |

FOREIGN PATENT DOCUMENTS

| | | | |
|---|---|---|---|
| JP | 2005-152403 | A | 6/2005 |
| JP | 2007-175185 | A | 7/2007 |
| JP | 2007-275483 | A | 10/2007 |
| JP | 2010-252836 | A | 11/2010 |
| JP | 3171697 | U | 11/2011 |
| JP | 3174209 | U | 3/2012 |
| JP | 2013-202296 | A | 10/2013 |
| JP | 6031859 | B2 | 11/2016 |
| JP | 6098237 | B2 | 3/2017 |

OTHER PUBLICATIONS

International Preliminary Report (IPRP) and its citations, issued for International Application No. PCT/JP2021/025667, Dated Jan. 31, 2022.
Chinese Office Action Issued for Corresponding Foreign Application No. 202180044927.3, Dated Dec. 24, 2024.
International Preliminary Report on Patentability, for International Application PCT/JP2021/025667, Dated Jan. 31, 2022.
Indian Office Action Issued for Corresponding Foreign Application No. 202217077167, Dated Sep. 1, 2023.

* cited by examiner

BLOOD PRESSURE CUFF

CROSS-REFERENCE TO RELATED APPLICATIONS

This application is the U.S. national stage application filed pursuant to 35 U.S.C. 365(c) and 120 as a continuation of International Patent Application No. PCT/JP2021/025667, filed Jul. 7, 2021, which application claims priority to Japanese Patent Application No. 2020-126733 filed Jul. 27, 2020, and Japanese Patent Application No. 2021-030092 filed Feb. 26, 2021, which applications are incorporated herein by reference in their entireties.

TECHNICAL FIELD

The present invention relates to a blood pressure cuff used in a sphygmomanometer for measuring blood pressure.

BACKGROUND ART

JP 06031859 B discloses a folding-back type compression band for a blood pressure measurement device. The compression band for the blood pressure measurement device has a configuration in which a hook-and-loop fastener is sewn on a front surface of an outer bag that stores an air bag. The outer bag of the compression band for the blood pressure measurement device is formed by welding an outer member and an inner member. At one end of the compression band for the blood pressure measurement device, a ring member through which the other end of the compression band for the blood pressure measurement device is passed and folded back is provided. A portion of the ring member is held between the outer member and the inner member. Further, the ring member is supported by the outer bag by folding back and sewing the one end of the compression band for the blood pressure measurement device to the inner member side.

JP 06098237 B describes a blood pressure cuff. This blood pressure cuff includes a bag-shaped band formed by welding a raised outer cloth and an inner cloth. The inner cloth is provided with a hook-and-loop fastener. A ring member for passing one end of the band therethrough is attached to the outer cloth by a ring attachment member. The ring attachment member is formed by folding back the same cloth material as the outer cloth so as to surround one side of the ring member and sewing the folded back portion on the remaining flat portion. A visible portion on the front side of the ring attachment member is raised to be engageable with the hook-and-loop fastener. A configuration is disclosed in which a flat portion of the ring attachment member is welded to the outer cloth.

SUMMARY OF INVENTION

Technical Problem

As in JP 06031859 B and JP 06098237 B, in the configuration of the band provided with the ring member, a region in which a plate-like member having a certain degree of rigidity is embedded may be provided on the outer side of the ring member in a longitudinal direction of the band. This region is provided in order to prevent the ring member from coming into direct contact with a target measurement site and to improve wearability when the band is worn. However, in some cases, this region enters a gap of the ring member or goes inward so as to be bent when the band is worn. As a result, wearing the band may cause pain.

The purpose of the present invention is to provide a blood pressure cuff that is easy to use and does not cause pain due to a terminal region of a band when the blood pressure cuff is worn.

Solution to Problem (1)

A blood pressure cuff including a band enveloping a fluid bag between a first skin member and a second skin member facing the first skin member; a ring-like member held at a position near one end edge in a longitudinal direction of the band and extending in a lateral direction of the band; and an auxiliary member stored inside a terminal region between the one end edge in the longitudinal direction of the band and the ring-like member and extending in the lateral direction, wherein the first skin member and the second skin member in the terminal region are welded or bonded to each other in a state where the auxiliary member is sandwiched between the first skin member and the second skin member.

Since the first skin member and the second skin member in the terminal region near the ring-like member are welded or bonded in a state where the auxiliary member is sandwiched between the first skin member and the second skin member, it is possible to increase the rigidity of the terminal region. As a result, it is possible to prevent the terminal region from passing through the ring-like member. Therefore, it is possible to prevent a target measurement site from being compressed in a state where the ring-like member is in contact with the target measurement site. In addition, it is possible to reduce the number of sewn portions at an end portion on one side in the longitudinal direction of the band by welding or bonding. This not only improves durability and productivity but also enhances appearance quality.

The blood pressure cuff includes a welded region or a bonded region of the first skin member and the second skin member in the terminal region formed surrounding the auxiliary member.

The welded region or the bonded region is formed in the terminal region, surrounding the auxiliary member, so that it is possible to effectively increase the rigidity of the terminal region.

In one embodiment, the ring-like member is attached in a state where the ring-like member is sandwiched between the first skin member and the second skin member, and the first skin member and the second skin member are further welded or bonded to each other in an adjacent region adjacent to the ring-like member on a side opposite to the terminal region with the ring-like member sandwiched between the adjacent region and the terminal region.

The ring-like member is surrounded and held by the terminal region and the adjacent region formed by welding or bonding. Thus, it is possible to attach the ring-like member while reducing the gap for holding the ring-like member, and the movable range of the ring-like member can be sufficiently narrowed. As a result, it is possible to more strongly prevent the terminal region from passing through the ring-like member.

In one embodiment, a width of the terminal region in the longitudinal direction is larger than a width of a gap between the band and the ring-like member located outside the band.

Since the width of the terminal region is larger than the width of the gap, it is possible to more strongly prevent the terminal region from passing through the ring-like member.

In one embodiment, a surface of the first skin member on a side of the auxiliary member in the terminal region and the auxiliary member are fixed to each other.

It is possible to suppress occurrence of stick-slip between the first skin member and the auxiliary member and improve accuracy of blood pressure measurement.

In one embodiment, the first skin member is a member on a side to be not in contact with a target measurement site in a state where the band is wound around and fixed to the target measurement site, and the second skin member is a member on a side to be in contact with the target measurement site in the state.

It is possible to suppress occurrence of stick-slip between the first skin member and the auxiliary member and improve the accuracy of blood pressure measurement.

Advantageous Effects of Invention

According to the present invention, it is possible to provide a blood pressure cuff which is easy to use and does not cause pain due to a terminal region of a band when the blood pressure cuff is worn.

BRIEF DESCRIPTION OF DRAWINGS

Various embodiments are disclosed, by way of example only, with reference to the accompanying schematic drawings in which corresponding reference symbols indicate corresponding parts, in which.

DESCRIPTION OF EMBODIMENTS

Overview of Biological Sound Measurement Device of Embodiment

First, an outline of an embodiment of a blood pressure cuff of the present invention will be described. In the blood pressure cuff of the embodiment, a terminal region between the ring-like member held near an end edge of a band and this end edge is formed by welding with an auxiliary member inside the terminal region. As a result, rigidity of the terminal region is increased to prevent the terminal region from passing through the ring-like member, thereby improving wearability of the band.

Hereinafter, a specific configuration example of the blood pressure cuff of the embodiment will be described. Various methods such as thermal welding, high-frequency welding, and ultrasonic welding can be employed as the welding method of the two members described below.

Embodiment

Figure 1:
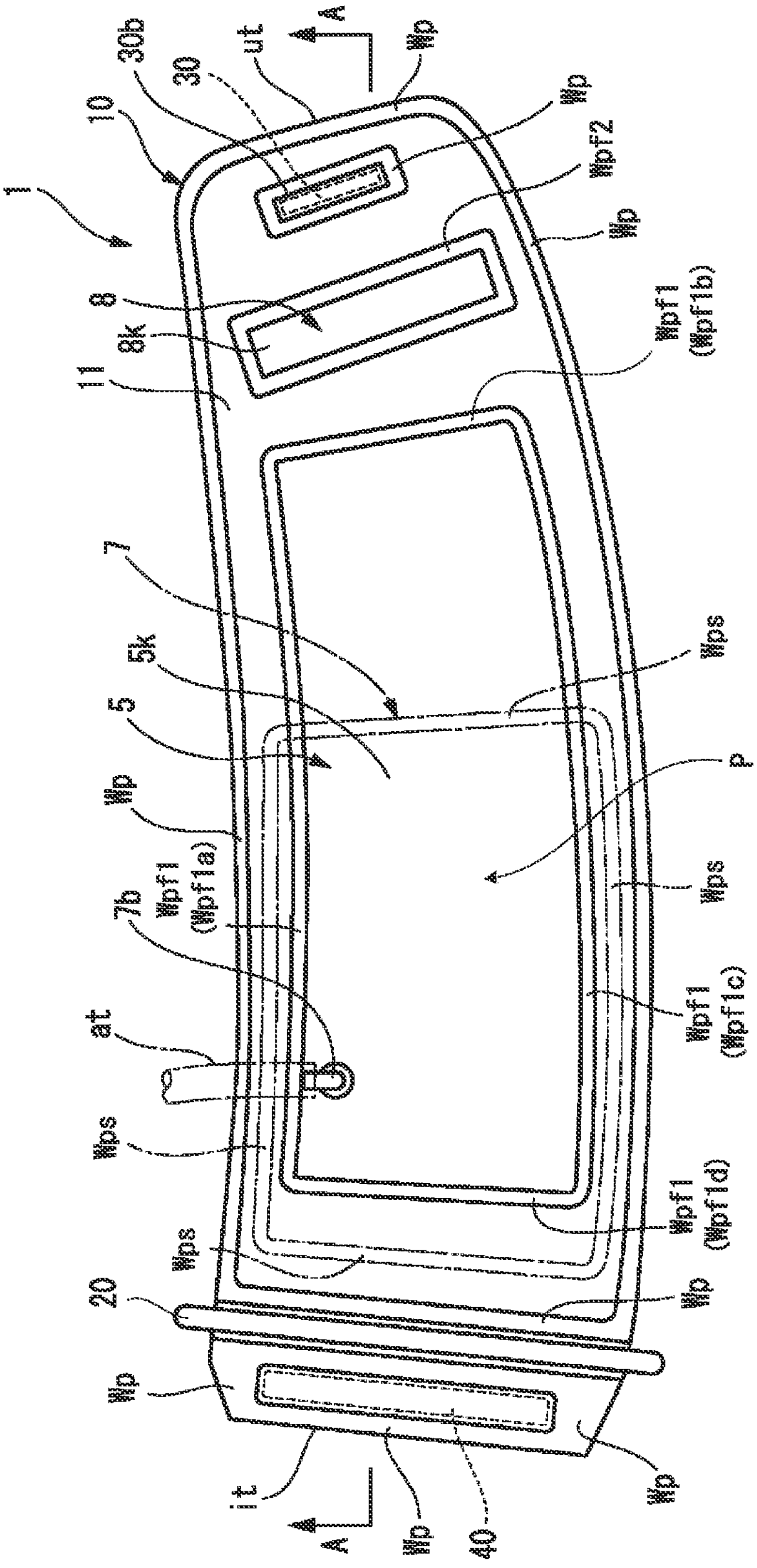
FIG. 1 is a plan view of a blood pressure cuff according to an embodiment of the present invention when viewed from a direction of an outer surface.
Figure 2:
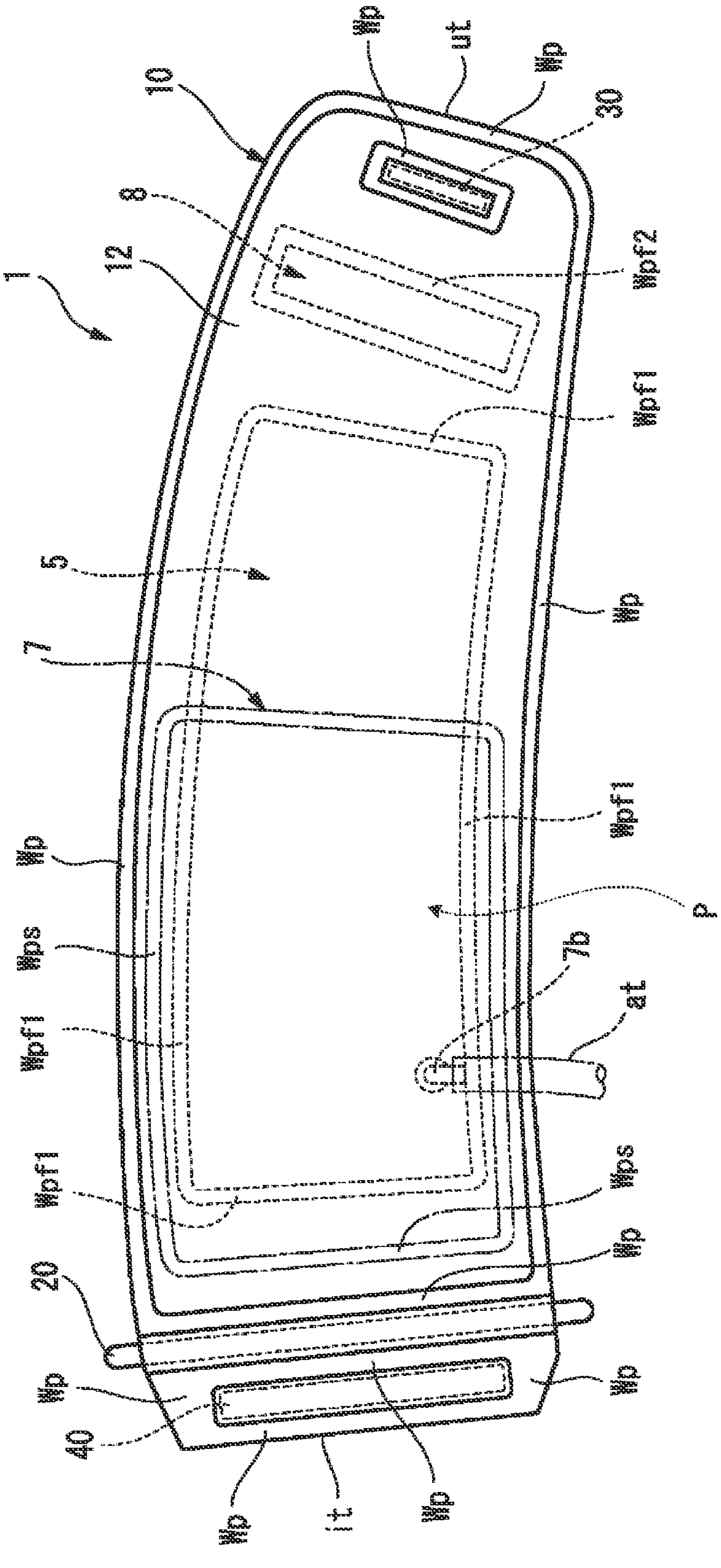
FIG. 2 is a plan view of the blood pressure cuff illustrated in FIG. 1 when viewed from a direction of an inner surface.
Figure 3:
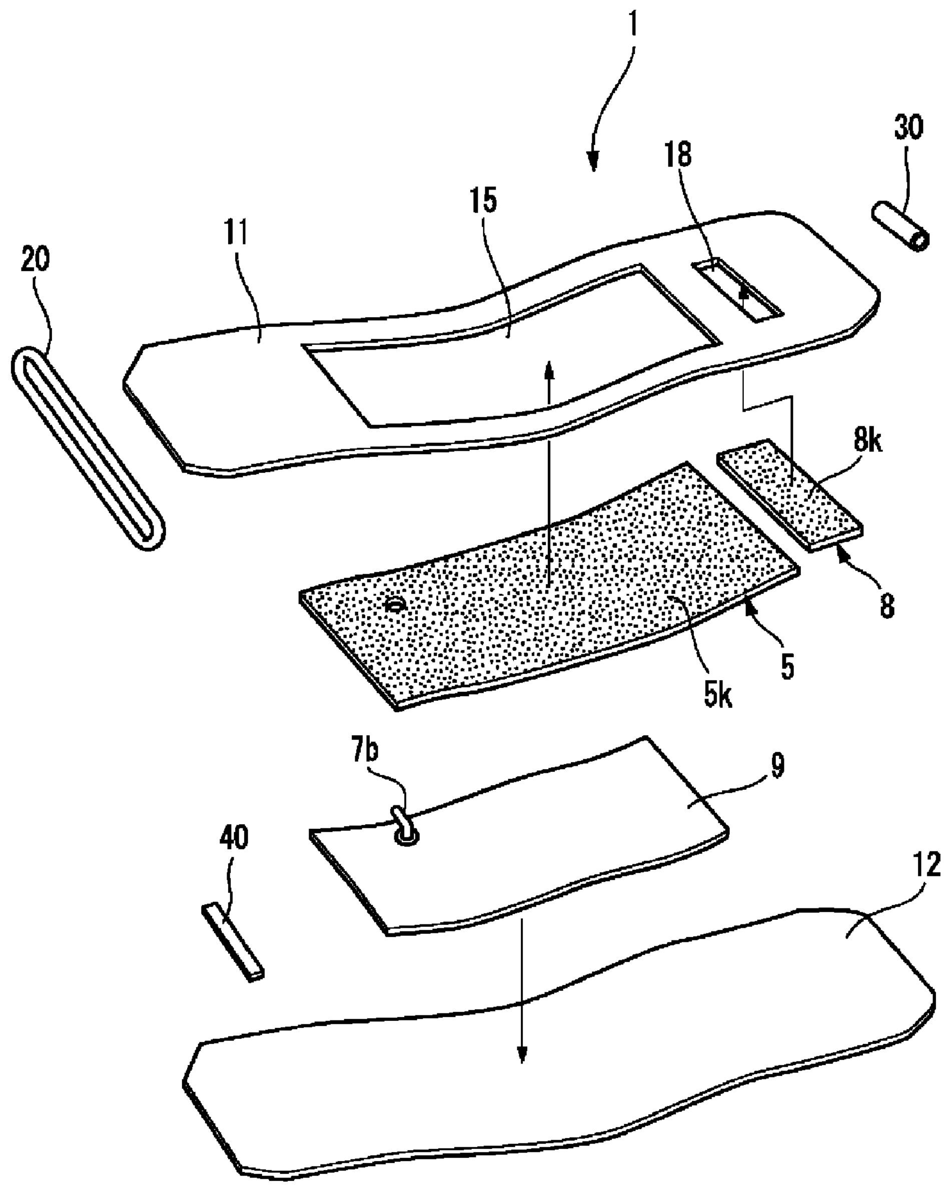
FIG. 3 is an exploded perspective view of the blood pressure cuff illustrated in FIG. 1.
Figure 4:
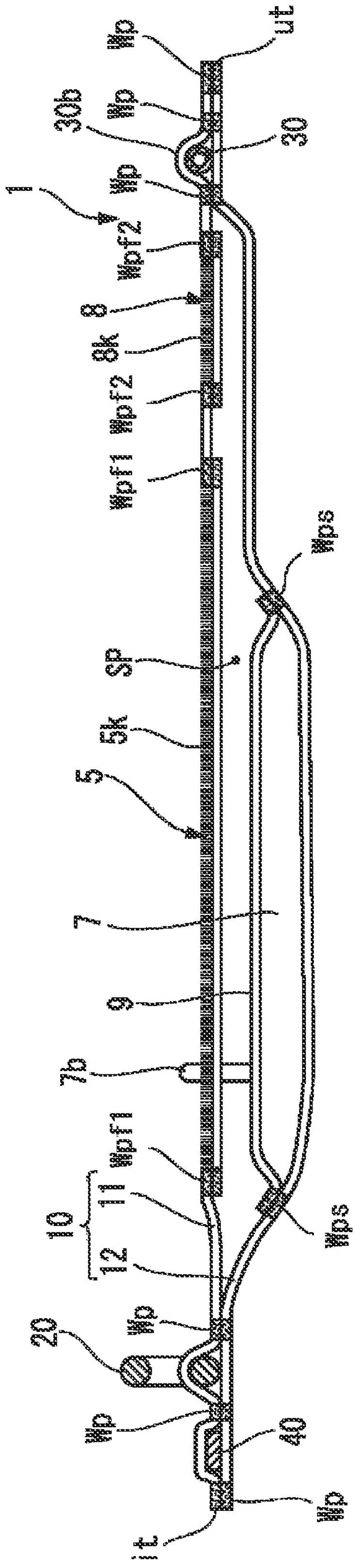
FIG. 4 is a cross-sectional view of a portion taken along line A-A of FIG. 1.
Figure 5:
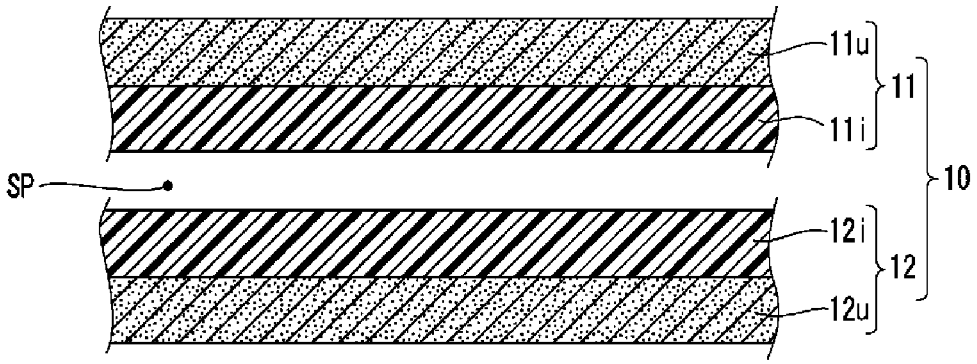
FIG. 5 is an enlarged cross-sectional view of an outer cloth and an inner cloth of the blood pressure cuff illustrated in FIG. 1.

FIG. 1 is a plan view of a blood pressure cuff 1 according to an embodiment of the present invention when viewed from a direction of an outer surface. FIG. 2 is a plan view of the blood pressure cuff 1 illustrated in FIG. 1 when viewed from a direction of an inner surface. FIG. 3 is an exploded perspective view of the blood pressure cuff 1 illustrated in FIG. 1. FIG. 4 is a cross-sectional view of a portion taken along line A-A of FIG. 1. FIG. 5 is an enlarged cross-sectional view of an outer cloth 11 and an inner cloth 12 of the blood pressure cuff 1 illustrated in FIG. 1.

As illustrated in FIGS. 1 and 2, the blood pressure cuff 1 includes a band 10 including an outer cloth 11 constituting a first skin member and an inner cloth 12 constituting a second skin member and facing the outer cloth 11. The outer cloth 11 and the inner cloth 12 are partly fixed to each other to form a storage space SP (see FIG. 4) therebetween. An air bag 7 constituting a fluid bag is stored in the storage space SP. The fluid bag is a bag that can be supplied with and discharge a fluid such as air and is inflated by the supply of the fluid. The air bag 7 can be supplied with and discharge air as a fluid.

Figure 12:
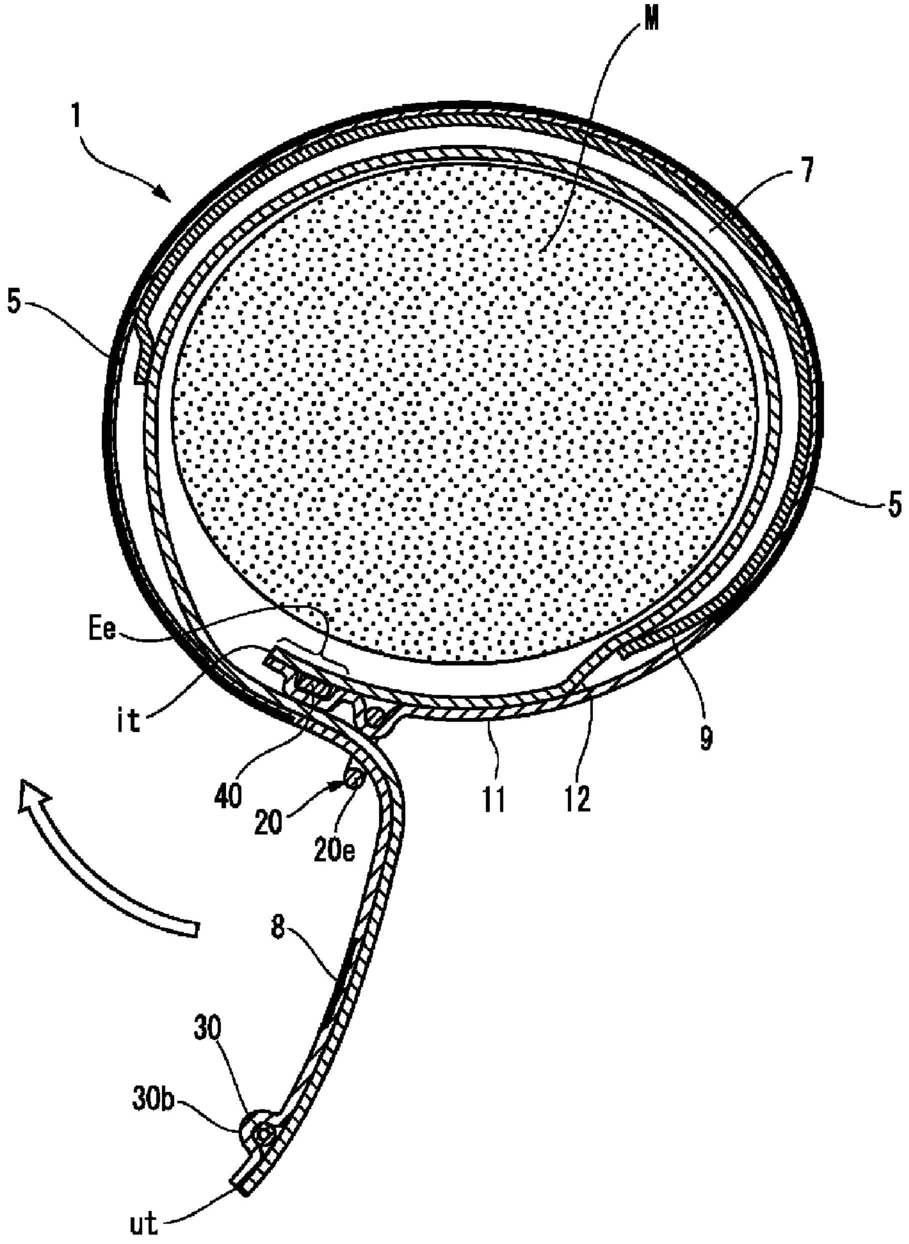
FIG. 12 is a schematic cross-sectional view illustrating a state where the blood pressure cuff illustrated in FIG. 1 is being worn on a target measurement site.

The band 10 has a band shape extending in a circumferential direction of an upper arm part M, which is a target measurement site, in a state of being wound around the upper arm part M (see FIG. 12). The circumferential direction in this state is a longitudinal direction of the band 10, and an axial direction of the upper arm part M is a lateral direction (width direction) of the band 10. Hereinafter, the longitudinal direction of the band 10 is also simply referred to as a longitudinal direction, and the lateral direction of the band 10 is also simply referred to as a lateral direction.

The inner cloth 12 constitutes a surface on a side to be in contact with the upper arm part M in a state where the band 10 is worn on the upper arm part M illustrated in FIG. 12. The outer cloth 11 constitutes a surface opposite to the upper arm part M side in the state where the band 10 is worn on the upper arm part M illustrated in FIG. 12. In the present embodiment, one end edge of the band 10 in the longitudinal direction is referred to as an end edge it, and the other end edge of the band 10 in the longitudinal direction is referred to as an end edge ut. The outer cloth 11 and the inner cloth 12 are joined together at their peripheries by welding as will be described later to form an exterior bag body, and the air bag 7 is located therein. In the present embodiment, a region where the outer cloth 11 and the inner cloth 12 are welded to each other is indicated by a welded region Wp. The welded region Wp constitutes a first welded region.

As illustrated in FIG. 5, each of the outer cloth 11 and the inner cloth 12 has, for example, a multi-layer structure. The inner cloth 12 includes a first member 12*u* having a sheet-like shape and made of a polyester cloth, a nylon cloth, or the like knitted with high stretchability to compress the target measurement site, and a second member 12*i* having a sheet-like shape, made of a PVC (polyvinylchloride) film or the like, and bonded to the inner side (storage space SP side) of the first member 12*u*. The first member 12*u* constitutes a surface member. The second member 12*i* constitutes a rear surface member.

The outer cloth 11 includes a sheet-like first member 11*u* made of a polyester cloth, a nylon cloth, or the like knitted with extremely low stretchability (with substantially no stretchability) as compared with the inner cloth 12, and a sheet-like second member 11*i* made of a PVC film or the like and bonded to the inner side (storage space SP side) of the first member 11*u*. Each of the outer cloth 11 and the inner cloth 12 has a multi-layer structure, which is effective for adjusting the stretchability and strength of each of the outer cloth 11 and the inner cloth 12.

Each of the second member 11*i* of the outer cloth 11 and the second member 12*i* of the inner cloth 12 may be made of a material suitable for welding. Examples of such a material include a material containing a resin such as a thermoplastic resin. The welded region Wp described above is a region formed by welding the second member 11*i* and the second member 12*i*.

As illustrated in FIG. 3, the blood pressure cuff 1 has a configuration in which a first hook-and-loop fastener 5, a second hook-and-loop fastener 8 having a smaller planar area than the first hook-and-loop fastener 5, a bag sheet member 9 with which the air bag 7 is formed, an oblong ring-like member 20, a tubular stopper tube 30, and a plate-like auxiliary member 40 are incorporated between the outer cloth 11 and the inner cloth 12.

In the outer cloth 11, a first opening portion 15 which is a rectangular opening and a second opening portion 18 which is a rectangular opening smaller than the first opening portion 15 are formed. The shape of each of the first opening portion 15 and the second opening portion 18 is rectangular, but is not limited thereto, and any shape can be adopted. The second opening portion 18 is provided in the vicinity of the end edge ut of the band 10. The first opening portion 15 is provided between the second opening portion 18 and the end edge it of the band 10. As illustrated in FIG. 4, the first opening portion 15 and the second opening portion 18 are formed in a portion of the outer cloth 11 that forms the storage space SP.

The first opening portion 15 is correspondingly provided with the first hook-and-loop fastener 5. The first hook-and-loop fastener 5 is welded to the outer cloth 11 in a state where the first opening portion 15 is closed from the storage space SP side.

In the present specification, a region of the outer cloth 11 to which the first hook-and-loop fastener 5 is welded is referred to as a welded region Wpf1. In the example of FIGS. 1 and 2, the welded region Wpf1 has a substantially rectangular frame shape. The welded region Wpf1 constitutes a third welded region.

A portion of the welded region Wpf1 extending in the lateral direction at an end portion on the end edge ut side is referred to as a welded region Wpf1*b*. A portion of the welded region Wpf1 extending in the lateral direction at an end portion on the end edge it side is referred to as a welded region Wpf1*d*. Portions of the welded region Wpf1 extending in the longitudinal direction at both end portions in the lateral direction are referred to as welded regions Wpf1*a* and Wpf1*c*.

A raised surface 5*k*, which is a fastener surface, is formed on the surface of the first hook-and-loop fastener 5. The first hook-and-loop fastener 5 is welded to the outer cloth 11 from the inner side (storage space SP side) of the band 10, in a state where the raised surface 5*k* of the first hook-and-loop fastener 5 is exposed through the first opening portion 15.

The second opening portion 18 is correspondingly provided with the second hook-and-loop fastener 8. The second hook-and-loop fastener 8 is welded to the outer cloth 11 in a state where the second opening portion 18 is closed from the storage space SP side. In the present specification, a region of the outer cloth 11 to which the second hook-and-loop fastener 8 is welded is indicated by a welded region Wpf2. In the example of FIGS. 1 and 2, the welded region Wpf2 has a substantially rectangular frame shape.

A hook surface 8*k* is formed on the surface of the second hook-and-loop fastener 8, as a fastener surface engageable with the raised surface 5*k*. The second hook-and-loop fastener 8 is welded to the outer cloth 11 from the inner side of the band 10 in a state where the hook surface 8*k* of the second hook-and-loop fastener 8 is exposed through the second opening portion 18. The area of the raised surface 5*k* exposed through the first opening portion 15 of the first hook-and-loop fastener 5 is larger than the area of the hook surface 8*k* exposed through the second opening portion 18 of the second hook-and-loop fastener 8.

As described above, the first hook-and-loop fastener 5 and the second hook-and-loop fastener 8 are provided such that the raised surface 5*k* and the hook surface 8*k* are exposed to the outer surface side of the band 10. When the band 10 is folded back on the end edge ut side and wound around the upper arm part M by using the ring-like member 20, the first hook-and-loop fastener 5 and the second hook-and-loop fastener 8 can be engaged with each other.

As illustrated in FIG. 4, the bag sheet member 9 is welded to the surface of the inner cloth 12 on the storage space SP side (the second member 12*i* described above). The bag sheet member 9 is a sheet-like member made of a highly stretchable material. The material of the bag sheet member 9 is not particularly limited, but a material containing a resin is preferably used; for example, PVC can be more preferably used.

An edge portion of the bag sheet member 9 is welded to the inner surface (the second member 12*i*) of the inner cloth 12 over the entire circumference, at a predetermined position with respect to the inner cloth 12. As a result, an airtight space is formed by the bag sheet member 9 and the inner cloth 12. This airtight space functions as the air bag 7. In the present specification, a region of the inner cloth 12 to which the bag sheet member 9 is welded is referred to as a welded region Wps. In the example of FIGS. 1 and 2, the welded region Wps has a substantially rectangular frame shape. The welded region Wps constitutes a second welded region. As illustrated in FIGS. 1 and 2, the welded region Wps is formed on the inner side of the welded region Wp of the outer cloth 11 and the inner cloth 12 that form the storage space SP.

The bag sheet member 9 is provided with a tube connecting portion 7*b* through which air can be supplied to and discharged from the airtight space. The tube connecting portion 7*b* is a portion to which an air tube at connected to a main body (not illustrated) of a sphygmomanometer is connected.

The bag sheet member 9 is disposed eccentrically to the end edge inside the storage space SP. In the band 10, the first hook-and-loop fastener 5 is provided on the end edge inside and has a large area. Therefore, as illustrated in FIGS. 1 and 2, the first hook-and-loop fastener 5 has an overlapped region P overlapping with the bag sheet member 9.

As illustrated in FIG. 1, the upper and lower portions (the welded region Wpf1*a* and the welded region Wpf1*c*) in the drawing extending in the longitudinal direction in the welded region Wpf1 (a substantially U-shaped portion in the example of the drawing) to the outer cloth 11 in the overlapped region P of the first hook-and-loop fastener 5 are positioned on the inner side, in the lateral direction, of the upper and lower portions in the drawing extending in the longitudinal direction in the welded region Wps. Furthermore, a portion (welded region Wpf1*d*) on the left side in the drawing extending in the lateral direction in the welded region Wpf1 to the outer cloth 11 in the overlapped region P of the first hook-and-loop fastener 5 is positioned on the inner side of the welded region Wps. That is, most of the welded region Wpf1 in the overlapped region P is located on the inner side of the welded region Wps and has almost no overlap with the welded region Wps.

Figure 6:
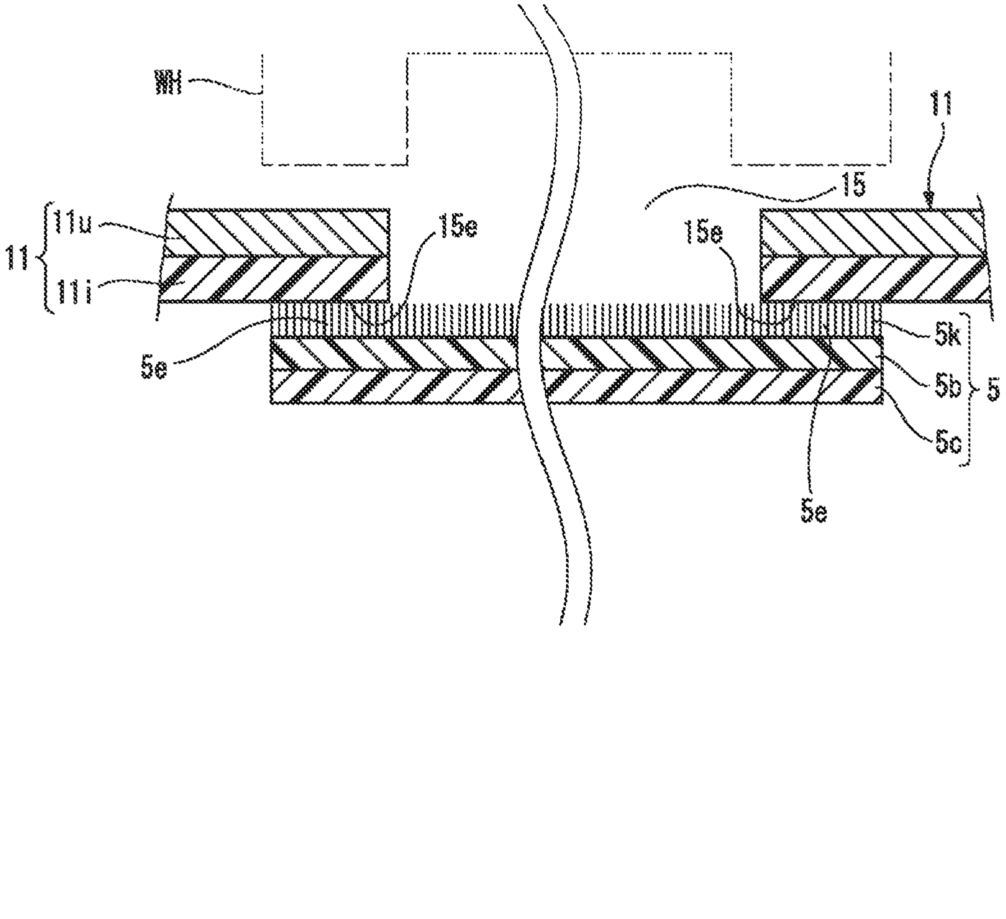
FIG. 6 is an enlarged schematic cross-sectional view illustrating a state before a first hook-and-loop fastener is welded in manufacturing the blood pressure cuff illustrated in FIG. 1.

FIG. 6 is an enlarged schematic cross-sectional view illustrating a state before the first hook-and-loop fastener 5 is welded in manufacturing the blood pressure cuff 1.

As illustrated in FIG. 6, in the first hook-and-loop fastener 5, in a state immediately before welding, an edge side portion 5*e* of the raised surface 5*k* faces an opening edge portion 15*e* of the first opening portion 15. In this state, welding is performed by applying a predetermined pressure to the outer cloth 11 by a welding head WH of a welding machine. That is, in a state where the edge side portion 5*e* of the raised surface 5*k* and the second member 11*i* of the opening edge portion 15*e* are pressed with a predetermined pressure, the second member 11*i* of the opening edge portion 15*e* is melted, and the edge side portion 5*e* of the raised surface 5*k* enters the melted portion of the second member 11*i*.

Figure 7:
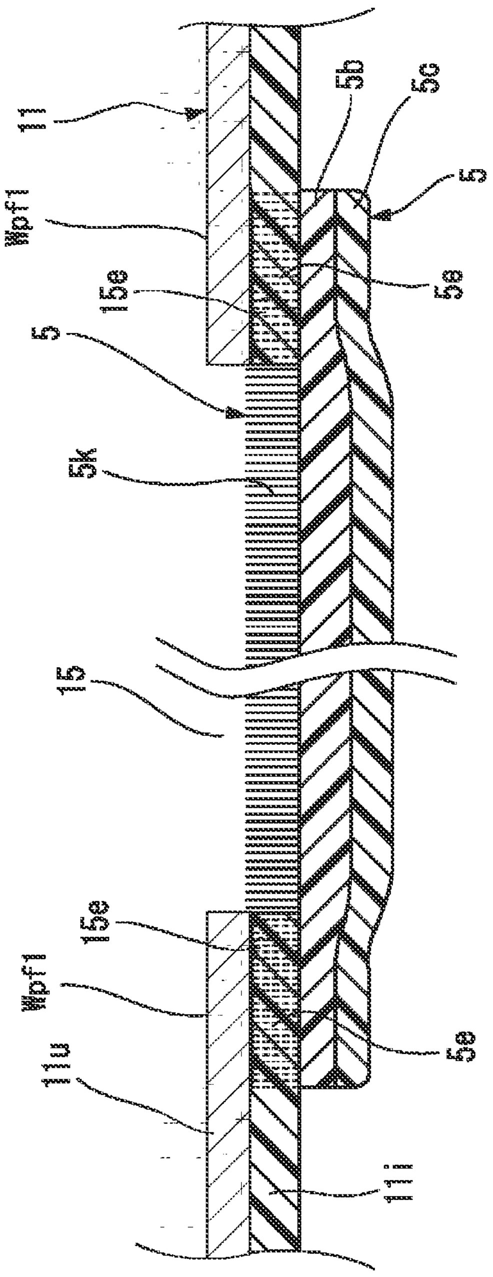
FIG. 7 is an enlarged schematic cross-sectional view illustrating a welded state of the first hook-and-loop fastener illustrated in FIG. 1.

FIG. 7 is an enlarged schematic cross-sectional view illustrating a welded state of the first hook-and-loop fastener 5 illustrated in FIG. 1. As illustrated in FIG. 7, the opening edge portion 15*e* of the first opening portion 15 and the edge side portion 5*e* of the raised surface 5*k* are in a welded state where the raised surface 5*k* sinks into the opening edge portion 15*e*. Therefore, in this welding, as can be seen from the structure of the raised surface 5*k*, the second member 11*i* is easily engaged with the raised surface 5*k*, the engagement area can be increased, and the engagement force can be made stronger, as compared with the normal welding between flat surfaces.

As illustrated in FIGS. 6 and 7, the first hook-and-loop fastener 5 has a configuration in which the raised surface 5*k* is formed on a fastener base 5*b* and a fastener rear surface member 5*c* is fixed to a surface of the fastener base 5*b* opposite to the raised surface 5*k* with an adhesive or the like. The position of the front edge face of the raised surface 5*k* on the side opposite to the fastener base 5*b* side is preferably closer to the outer surface side of the outer cloth 11 than the half-thickness position of the first member 11*u* of the outer cloth 11 is, and more preferably at the same position as the outer surface of the outer cloth 11. In this manner, the first hook-and-loop fastener 5 and the second hook-and-loop fastener 8 can be favorably joined to each other. In addition, the appearance quality of the cuff can be improved.

For the fastener rear surface member 5*c*, a raw material having stretchability equal to or lower than that of the first member 11*u* is used. For the fastener rear surface member 5*c*, for example, tarpaulin, polyester cloth, a PVC film, or the like can be used. Selecting the raw material of the fastener rear surface member 5*c* allows appropriate compensation for changes in the stretchability, strength, or the like of the outer cloth 11 due to the formation of the first opening portion 15 in the outer cloth 11.

Like the first hook-and-loop fastener 5, the second hook-and-loop fastener 8 may include a fastener rear surface member, but desirably has the following structure.

Figure 8:
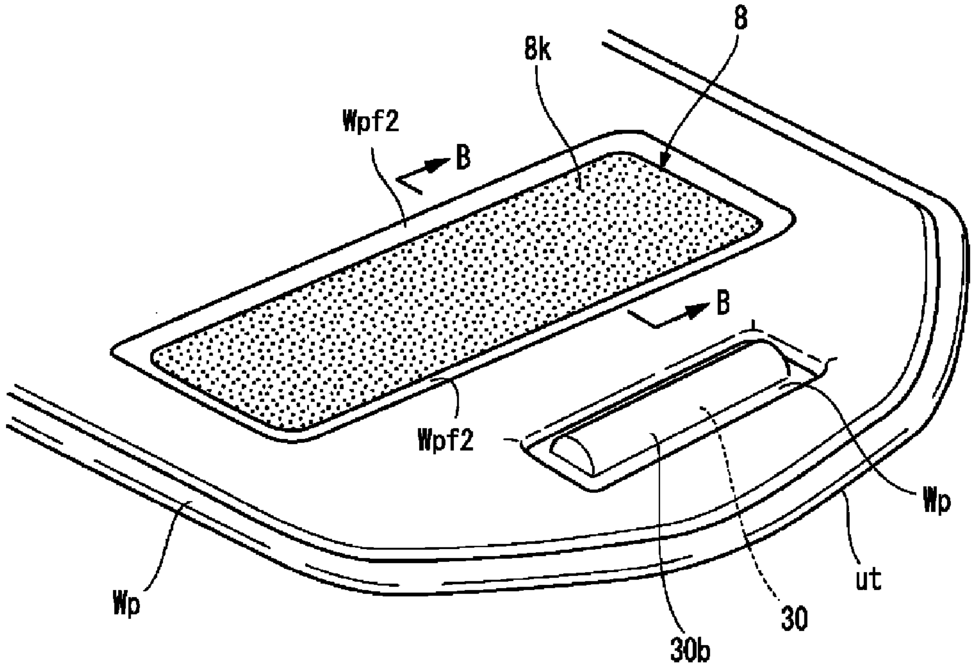
FIG. 8 is an enlarged perspective view illustrating an end portion on a side where a second hook-and-loop fastener is provided in the blood pressure cuff illustrated in FIG. 1.

FIG. 8 is an enlarged perspective view illustrating the end edge ut side of the blood pressure cuff 1 illustrated in FIG. 1. As illustrated in FIG. 8, on the inner side of the welded region Wpf2, the hook surface 8*k* of the second hook-and-loop fastener 8 is provided at substantially the same height as or slightly lower height than the welded region Wpf2. As will be described later, a stopper portion 30*b* on the side of the end edge ut of the band 10 is a thick portion necessary for preventing the end edge ut of the band 10 from coming off the ring-like member 20.

Figure 9:
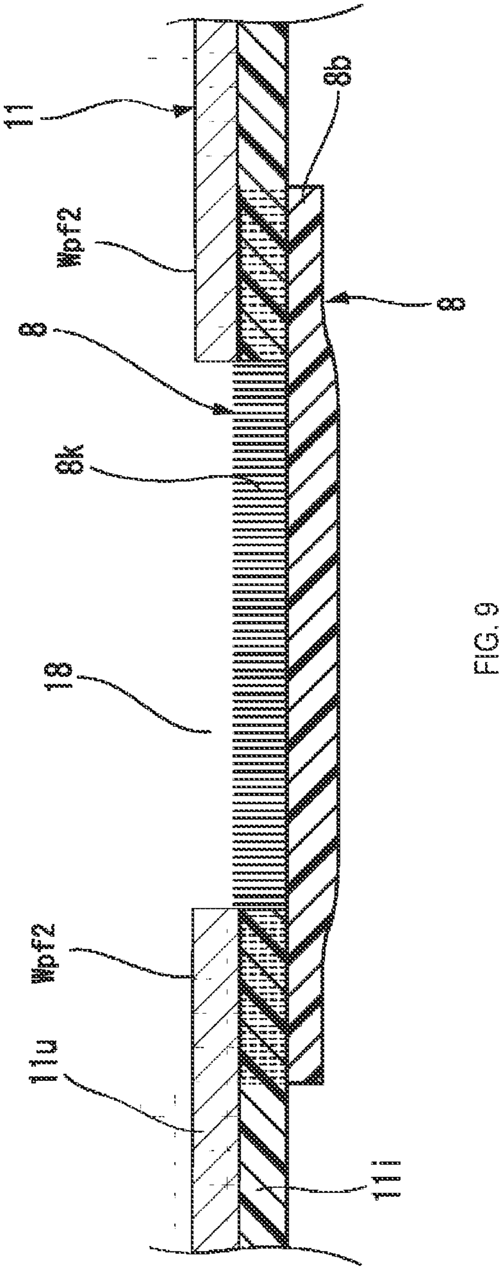
FIG. 9 is a cross-sectional view of a portion taken along line B-B of FIG. 8.

FIG. 9 is a cross-sectional view taken along line B-B of FIG. 8. As illustrated in FIG. 9, unlike the first hook-and-loop fastener 5, the second hook-and-loop fastener 8 has a structure in which a fastener rear surface member is not provided on the side opposite to the hook surface 8*k*. That is, the second hook-and-loop fastener 8 is constituted only by a fastener base member 8*b* on which the hook surface 8*k* is formed. In the second hook-and-loop fastener 8, as in the first hook-and-loop fastener 5, the edge side portion of the hook surface 8*k* of the outer cloth 11 in contact with the second member 11*i* is welded to the second member 11*i* and is firmly joined to the outer cloth 11. The position of the front edge face of the hook surface 8*k* on the side opposite to the fastener base member 8*b* side is preferably closer to the outer surface side of the outer cloth 11 than the half-thickness position of the first member 11*u* of the outer cloth 11 is, and more preferably at the same position as the outer surface of the outer cloth 11. In this manner, the first hook-and-loop fastener 5 and the second hook-and-loop fastener 8 can be favorably joined to each other. In addition, the appearance quality of the cuff can be improved.

Figure 10:
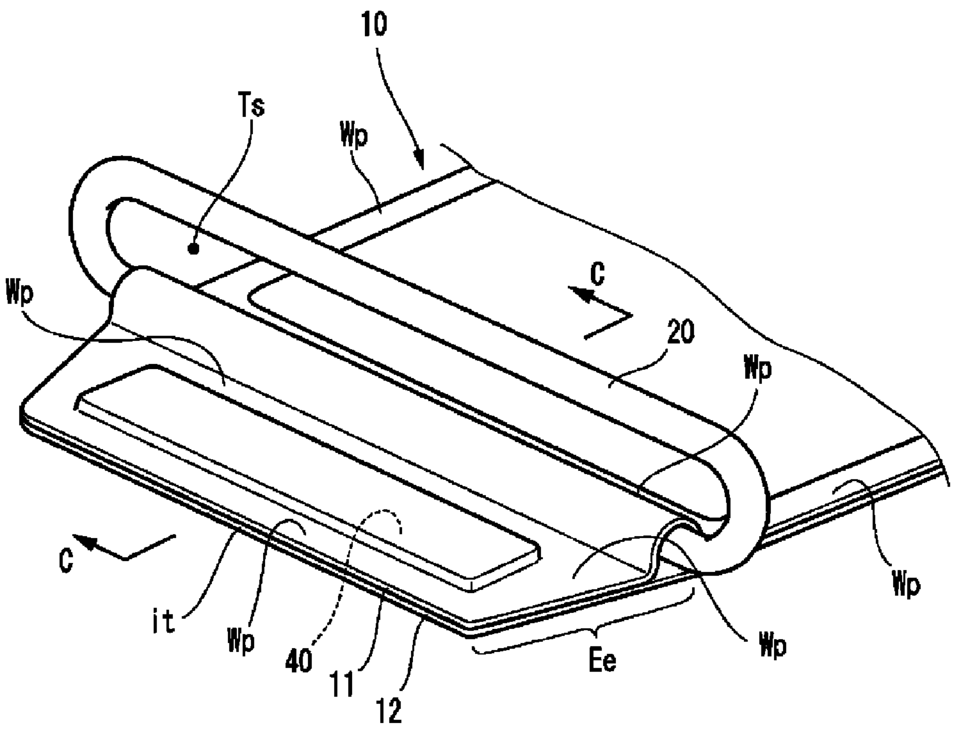
FIG. 10 is an enlarged perspective view illustrating a terminal region of the blood pressure cuff illustrated in FIG. 1.
Figure 11:
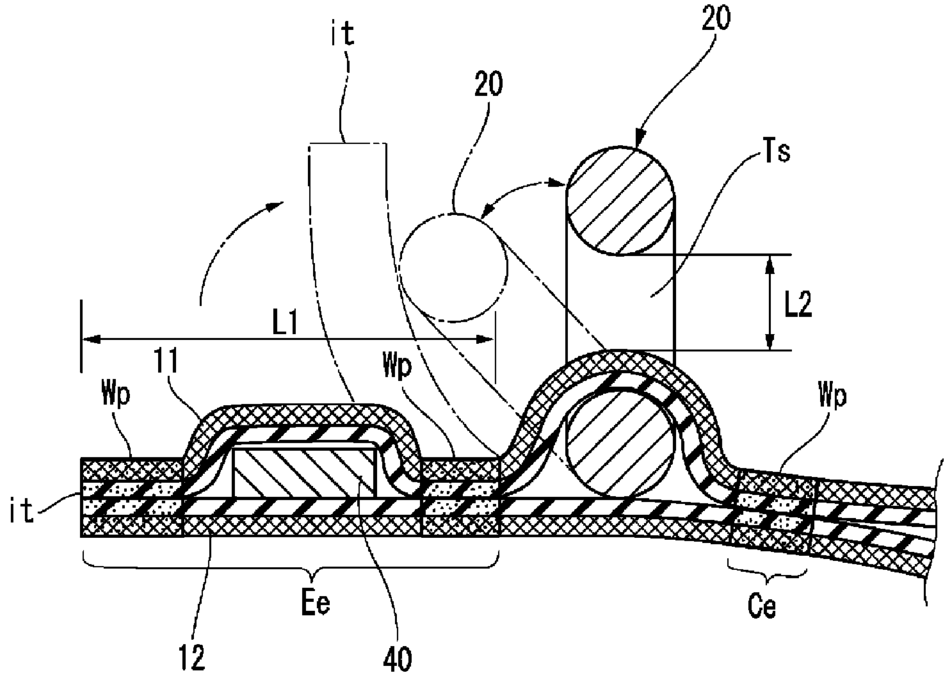
FIG. 11 is an enlarged cross-sectional view of a portion taken along line C-C of the terminal region illustrated in FIG. 10.

FIG. 10 is an enlarged perspective view illustrating the terminal region Ee of the blood pressure cuff 1. FIG. 11 is a cross-sectional view of a portion taken along line C-C of FIG. 10. As illustrated in FIG. 10, the ring-like member 20 is held on the band 10 at a position near the end edge it. Specifically, as illustrated in FIG. 11, the ring-like member 20 is attached to the band 10 with the ring-like member 20 sandwiched between the outer cloth 11 and the inner cloth 12. The ring-like member 20 has an oblong shape extending slightly larger than the width of the band 10 in the lateral direction of the band 10.

In the terminal region Ee between the end edge it of the band 10 and the ring-like member 20, there is provided an auxiliary member 40 having a rectangular plate shape in plan view and extending in the lateral direction substantially parallel to the ring-like member 20. The auxiliary member 40 is fixed so as to be sandwiched between the outer cloth 11 and the inner cloth 12. The four peripheral sides of the auxiliary member 40 are surrounded by the welded region Wp, and the auxiliary member 40 is firmly fixed so as not to move in the surrounded space. Here, the welded region Wp around the auxiliary member 40 is formed in the entire region of the terminal region Ee other than a portion where the auxiliary member 40 is disposed.

The region formed by welding the two members has higher rigidity than a configuration in which the two members are fixed by sewing. Although the raw material of the auxiliary member 40 is not particularly limited, the auxiliary member 40 is made of a raw material such as a synthetic resin, which is harder than the outer cloth 11. The entire portion of the terminal region Ee excluding the auxiliary member 40 is the welded region Wp, and further includes the auxiliary member 40, which is hard. Therefore, the terminal region Ee is formed as a region having higher rigidity than the other portion of the band 10.

As illustrated in FIG. 11, in the band 10, the periphery of the attachment portion of the ring-like member 20 is also constituted by the welded region Wp. That is, the outer cloth 11 and the inner cloth 12 are also welded to each other in an adjacent region Ce adjacent to the ring-like member 20 on the opposite side to the terminal region Ee with the ring-like member 20 therebetween.

In this manner, the ring-like member 20 is surrounded by the welded region Wp and is firmly attached so as not to move. The term "not to move" used here means that the ring-like member 20 can be swung around the attachment portion thereof, but the swing axis thereof does not move in the longitudinal direction of the band 10.

As illustrated in FIG. 11, the terminal region Ee is formed such that a width L1 in the longitudinal direction of the band 10 is larger than a width L2 of a gap Ts between the ring-like member 20 located outside the band 10 and the front surface of the band 10. Therefore, it is possible to make the end edge it of the band 10 difficult to enter the gap Ts when the terminal region Ee moves to the ring-like member 20 side or when the ring-like member 20 moves to the terminal region Ee side.

Manufacturing Process of Blood Pressure Cuff 1

Hereinafter, an example of manufacturing the blood pressure cuff 1 will be described. In this case, the manufacture can be performed by welding components illustrated in FIG. 3 as described below.

The welding step on the outer cloth 11 side will be described. First, the first hook-and-loop fastener 5 is set in a welding machine such that the first opening portion 15 is closed by the first hook-and-loop fastener 5 with the raised surface 5*k* facing upward and with the outer cloth 11 overlapping with the first hook-and-loop fastener 5. In this state, the second member 11*i* and the raised surface 5*k* of the first hook-and-loop fastener 5 in the opening edge portion 15*e* (see FIG. 6) of the first opening portion 15 are welded to each other. Subsequently, the second hook-and-loop fastener 8 is also welded to the outer cloth 11 like the first hook-and-loop fastener 5.

The welding step on the inner cloth 12 side will be described. First, the tube connecting portion 7*b* is welded to a predetermined position of the bag sheet member 9. Subsequently, the bag sheet member 9 is welded to the inner surface side of the inner cloth 12. The position of the welded region Wps of the bag sheet member 9 is considered such that the welded region Wps does not overlap with the welded region Wp of the band 10 and most of the welded region Wpf1 of the first hook-and-loop fastener 5. For example, the width dimension of the bag sheet member 9 in the lateral direction of the band 10 is set so as to be positioned on the outer side of the welded region Wpf1 of the first hook-and-loop fastener 5 in the lateral direction. Accordingly, the welded region Wps along the longitudinal direction of the band 10 can be positioned between the welded region Wpf1 of the first hook-and-loop fastener 5 and the welded region Wp of the outer edge of the band 10. As a result, the welded region Wp, the welded region Wps, and the welded region Wpf1, which extend in the longitudinal direction of the band 10, are prevented from overlapping with each other in the thickness direction of the band 10. Since the plurality of welded regions each having rigidity and extending in the longitudinal direction do not overlap with each other, rigidity is prevented from being increased at a specific position of the band 10, and strangeness and discomfort caused by a cured portion when the band 10 is worn are avoided.

Next, the outer cloth 11 and the inner cloth 12 are set in a welding machine such that their inner surface sides face each other. In this state, the outer edges of the outer cloth 11 and the inner cloth 12 are welded. Here, the welding is performed in a region between the adjacent region Ce and the end edge ut.

Next, welding is performed in a portion between the ring-like member 20 and the end edge it (terminal region Ee). The welding is performed with the auxiliary member 40 inserted between the outer cloth 11 and the inner cloth 12. Thereafter, the stopper tube 30 inserted in advance between the outer cloth 11 and the inner cloth 12 is moved to a predetermined position on the end edge ut side, and then the outer periphery of the stopper tube 30 is welded to form the stopper portion 30*b*. Thus, the manufacturing process of the blood pressure cuff 1 is completed.

According to the above-described manufacturing process, the blood pressure cuff 1 has a configuration obtained without sewing in which all the fixed portions are formed of the welded regions. Specifically, in the storage space SP formed between the outer cloth 11 and the inner cloth 12, the first hook-and-loop fastener 5, the second hook-and-loop fastener 8, and the air bag 7 are fixed and stored by welding. Further, the ring-like member 20 and the auxiliary member 40 are attached to the end edge it side of the band 10 by welding. The stopper tube 30 is attached to the end edge ut side of the band 10 by welding. Thus, the entire assembly of the blood pressure cuff 1 is carried out only by welding.

FIG. 12 is a schematic cross-sectional view illustrating a state where the blood pressure cuff 1 is being worn on the upper arm part M. As illustrated in FIG. 12, when blood pressure is measured, the blood pressure cuff 1 is worn on the upper arm part M as the target measurement site. In this case, the end edge ut of the band 10 is passed through the ring-like member 20 in advance. That is, by making the stopper portion 30*b* pass through the gap Ts of the ring-like member 20, a loop shape of the band 10 is always maintained, and it is easy to wear the band 10 on the upper arm part M.

The arm is passed through the loop of the band 10 formed in this manner such that the air bag 7 is positioned at a predetermined position of the upper arm part M, and the portion of the band 10 through which the ring-like member 20 is passed is pulled so as to be folded back. Then, the band 10 is made to press the upper arm part M with a pressure as appropriate, and the second hook-and-loop fastener 8 is pressed against and fixed to the first hook-and-loop fastener 5. In this winding operation, unexpected bending is not caused to the terminal region Ee due to its rigidity, and the state where the inner surface thereof is in contact with the upper arm part M is maintained (the state illustrated in the drawing). Therefore, in a state where the winding is completed, the ring-like member 20 falls in the folding-back direction, a tip side 20*e* is always positioned on the outer side of the auxiliary member 40, so that the ring-like member 20 does not come into direct contact with the upper arm part M.

Effects of Blood Pressure Cuff 1

As described above, in the blood pressure cuff 1, the first hook-and-loop fastener 5 and the second hook-and-loop fastener 8 are provided on the inner side of the band 10. Thus, it is possible to prevent an object from being caught by the first hook-and-loop fastener 5 and the second hook-and-loop fastener 8 when the band 10 is worn, for example. As a result, it is possible to prevent the first hook-and-loop fastener 5 and the second hook-and-loop fastener 8 from being peeled off from each other and improve the durability of the blood pressure cuff 1.

Further, the first hook-and-loop fastener 5 and the second hook-and-loop fastener 8 are welded to the outer cloth 11. Therefore, the blood pressure cuff 1 can be easily manufactured and the manufacturing cost can be reduced as compared with the conventional sewing. Furthermore, as compared with a configuration in which the first hook-and-loop fastener 5 and the second hook-and-loop fastener 8 are fixed to the outer surface of the outer cloth 11 by sewing, the appearance quality of the blood pressure cuff 1 can be improved because the sewn portions and the fastener end edges are not visible.

In addition, in the blood pressure cuff 1, the first hook-and-loop fastener 5 and the second hook-and-loop fastener 8 can be welded to the outer cloth 11 using a material generally used as the outer cloth 11. Therefore, an existing raw material of the blood pressure cuff can be used as the band 10 as it is, and an increase in manufacturing cost can be prevented.

In the blood pressure cuff 1, the first hook-and-loop fastener 5 is provided with the fastener rear surface member 5*c* having stretchability equal to or lower than that of the first member 11*u* on the rear surface side of the surface exposed through the first opening portion 15. Accordingly, an increase in stretchability of the outer cloth 11 due to the formation of the first opening portion 15 can be suppressed by the fastener rear surface member 5*c*. As a result, it is possible to realize the compression state of the target measurement site suitable for blood pressure measurement.

In the blood pressure cuff 1, the fastener rear surface member 5*c* is provided on the rear surface side of the first hook-and-loop fastener 5 occupying a large proportion in the outer cloth 11. Therefore, the stretchability of the entire outer cloth 11 can be sufficiently and appropriately adjusted. As a result, it is possible to compress the target measurement site suitably for blood pressure measurement.

In addition, in the blood pressure cuff 1, the fastener rear surface member 5*c* is provided on the rear surface side of the first hook-and-loop fastener 5 on the side near the air bag 7 which greatly contributes to the compression of the target measurement site. This allows the stretchability of the outer cloth 11 in the vicinity of the air bag 7 to be adjusted to be suitable therefor. As a result, it is possible to compress the target measurement site suitably for blood pressure measurement.

In addition, in the blood pressure cuff 1, since the second hook-and-loop fastener 8 is not provided with a fastener rear surface member, it is possible to simplify the configuration and reduce the manufacturing cost without adding more members than necessary. The second hook-and-loop fastener 8 has a small area and is disposed near the end edge ut. Therefore, even when the stretchability of the outer cloth 11 is slightly increased at the portion of the second hook-and-loop fastener 8 of the band 10 due to the presence of the second opening portion 18, the influence on blood pressure measurement can be made slight.

In the blood pressure cuff 1, the outer cloth 11 and the inner cloth 12 in the terminal region Ee near the ring-like member 20 are welded to each other in a state where the auxiliary member 40 is sandwiched therebetween. Therefore, the rigidity of the terminal region Ee can be enhanced. As a result, it is possible to prevent the terminal region Ee from passing through the ring-like member 20. Therefore, it is possible to prevent a target measurement site from being compressed in a state where the ring-like member 20 is in contact with the target measurement site. Further, the conventional seamed portion at the end edge it of the band 10 can be reduced by welding, which not only improves durability and productivity, but also enhances appearance quality.

In particular, in the blood pressure cuff 1, since the welded region Wp is formed surrounding the auxiliary member 40 in the terminal region Ee, the rigidity of the terminal region Ee can be effectively increased.

In the blood pressure cuff 1, the ring-like member 20 is surrounded by the terminal region Ee and the adjacent region Ce and is held in the welded region Wp.

Thus, it is possible to attach the ring-like member 20 to the band 10 with a reduced gap for holding the ring-like member 20. Thus, the movable range of the ring-like member 20 can be sufficiently narrowed. As a result, it is possible to more strongly prevent the terminal region Ee from passing through the ring-like member 20.

In the blood pressure cuff 1, the width L1 of the terminal region Ee is larger than the width L2 of the gap Ts formed by the ring-like member 20. Therefore, it is possible to more strongly prevent the terminal region Ee from passing through the ring-like member 20.

In the blood pressure cuff 1, the air bag 7 is formed by welding the bag sheet member 9 to the inner cloth 12. Therefore, for example, a step of separately manufacturing the air bag is not necessary, and an operation of incorporating the air bag between the outer cloth 11 and the inner cloth 12 can also be eliminated. As a result, the number of components of the air bag 7 and the number of manufacturing steps of the blood pressure cuff 1 are reduced, so that the manufacturing cost thereof can be reduced.

In addition, in the blood pressure cuff 1, since the air bag 7 can be formed by welding to the inner cloth 12, the position where the air bag 7 is disposed can be flexibly determined. For example, as described above, the welded region Wp, the welded region Wps, and the welded region Wpf1, which extend in the longitudinal direction of the band 10, can be designed so as not to overlap with each other in the thickness direction of the band 10. Therefore, it is possible to improve the wearability of the band 10.

In the blood pressure cuff 1, the bag sheet member 9 with which the air bag 7 is formed is not fixed to the outer cloth 11. Therefore, the outer cloth 11 can be processed freely. As a result, it is possible to increase the degree of freedom in designing the cuff and to reduce the manufacturing cost. In the blood pressure cuff 1, the bag sheet member 9 is formed as a separate body from the outer cloth that and is not fixed to the outer cloth 11. Thus, noise transmitted from the outer cloth 11 side to the air bag 7 can be suppressed, and the accuracy of blood pressure measurement can be improved.

In the blood pressure cuff 1, the welded region Wpf1*d* of the welded region Wpf1 between the first hook-and-loop fastener 5 and the outer cloth 11 is located on the inner side of the welded region Wps. Thus, it is possible to prevent hardening of the band 10 in the overlapped region due to the welded region Wps and the welded region Wpf1*d* overlapping with each other. As a result, it is possible to improve the wearability of the band 10.

Modified Example of Blood Pressure Cuff 1

In the above-described embodiment, both the first hook-and-loop fastener 5 and the second hook-and-loop fastener 8 have been described as hook-and-loop fasteners. However, the first hook-and-loop fastener 5 and the second hook-and-loop fastener 8 only need to be engaged with each other, and one side may be a normal cloth having a simple raised structure. That is, the first member 11*u* of the outer cloth 11 may be formed of a cloth having a raised structure, and one hook-and-loop fastener engageable with the raised structure of the outer cloth 11 may be welded to the outer cloth 11. Further, in the above-described embodiment, for fastener surfaces, the first hook-and-loop fastener 5 is the raised surface 5*k* and the second hook-and-loop fastener 8 is the hook surface 8*k*; however, the present invention is not limited thereto, and a reverse configuration may be adopted.

In the above-described embodiment, the air bag 7 is formed by welding the bag sheet member 9 only to the inner cloth 12 of the outer cloth 11 and the inner cloth 12. However, a reverse configuration may be adopted. That is, the air bag 7 may be formed by welding the bag sheet member 9 only to the outer cloth 11 of the outer cloth 11 and the inner cloth 12. To be specific, the air bag 7 may be formed by welding the bag sheet member 9 to the second member 11*i* of the outer cloth 11. In this case, the welded region between the outer cloth 11 and the bag sheet member 9 may be provided at the same position as the welded region Wps of FIG. 2 in a plan view. In this configuration, the first hook-and-loop fastener 5 and the welded region Wps of the bag sheet member 9 partly overlap with each other. However, the fastener rear surface member 5*c* is included in the first hook-and-loop fastener 5. Therefore, in this overlapped portion, the bag sheet member 9 can be welded to the outer cloth 11 with the first hook-and-loop fastener 5 therebetween.

In the above-described embodiment, the ring-like member 20 is attached between the outer cloth 11 and the inner cloth 12, but the present invention is not limited thereto. For example, the ring-like member 20 may be held on the outer surface of the band 10 with another attachment member therebetween.

In the above-described embodiment, the outer cloth 11 and the inner cloth 12 in the terminal region Ee are welded to each other in a state where the auxiliary member 40 is sandwiched therebetween, but the present invention is not limited thereto. For example, the outer cloth 11 and the inner cloth 12 in the terminal region Ee may be bonded and fixed in a state where the auxiliary member 40 is sandwiched therebetween. Similarly, also in the adjacent region Ce, the outer cloth 11 and the inner cloth 12 may be bonded and fixed to each other. The range of the bonded region in this case is the same as that of the welded region Wp. As a bonding method, a method in which bonding is performed by applying an adhesive to one of the outer cloth 11 and the inner cloth 12, a method in which bonding is performed by heating in a state where a thermosetting tape is attached to one of the outer cloth 11 and the inner cloth 12, or the like can be employed.

Since the auxiliary member 40 of the blood pressure cuff 1 is accommodated in the space sealed by the outer cloth 11 and the inner cloth 12, the auxiliary member 40 does not easily move in the space. However, in order to more strongly prevent movement of the auxiliary member 40, the auxiliary member 40 and the outer cloth 11 are preferably fixed to each other. Hereinafter, this modified example will be described with reference to FIGS. 13 and 14.

Figure 13:
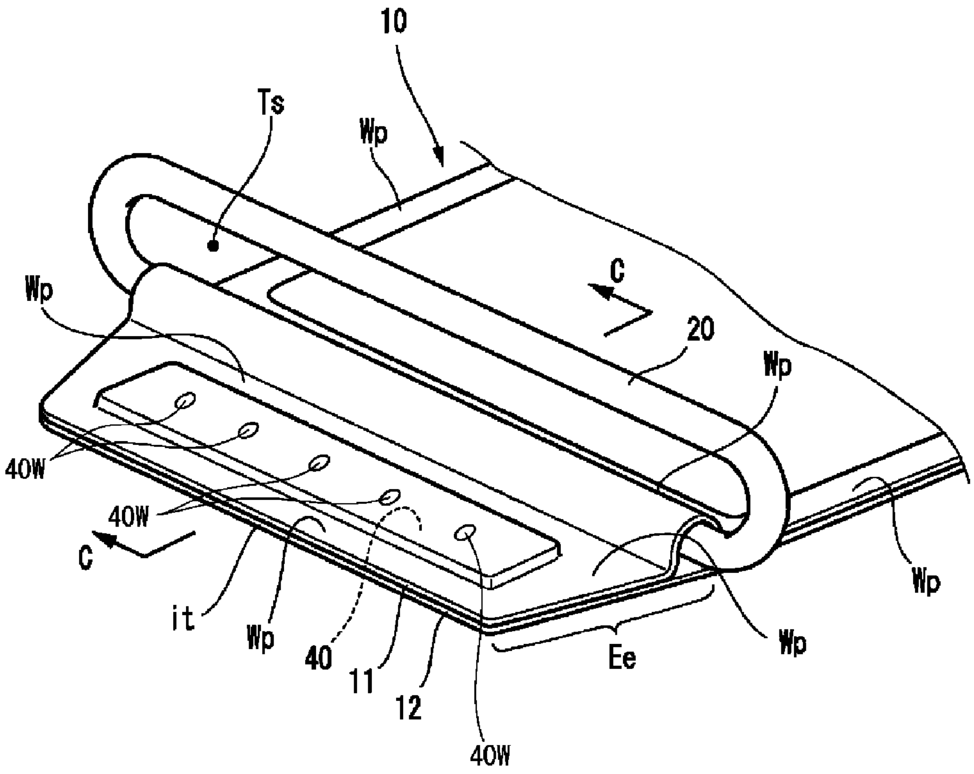
FIG. 13 is an enlarged perspective view illustrating a modified example of the terminal region of the blood pressure cuff illustrated in FIG. 1; and, FIG. 14 is an enlarged cross-sectional view of a portion taken along line C-C of the terminal region illustrated in FIG. 13.
Figure 14:
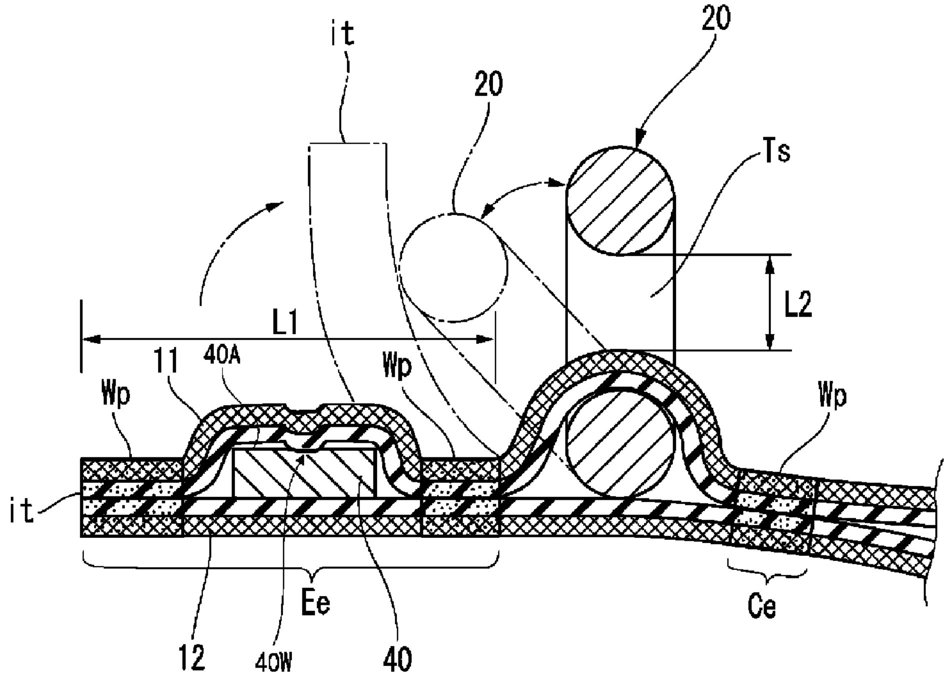

FIG. 13 is an enlarged perspective view illustrating a modified example of the terminal region Ee of the blood pressure cuff 1 illustrated in FIG. 1. FIG. 14 is an enlarged cross-sectional view of a portion taken along line C-C of the terminal region Ee illustrated in FIG. 13. The configuration in FIG. 13 is the same as that in FIG. 10 except that five fixing regions 40W are added to the terminal region Ee of the blood pressure cuff 1.

The fixing region 40W is a region in which a part of a region facing the auxiliary member 40 in the inner surface (second member 11*i* illustrated in FIG. 5) of the outer cloth 11 on the side fixed to the inner cloth 12 and the auxiliary member 40 are fixed to each other by welding, bonding, or the like. In the example of FIG. 13, five fixing regions 40W are provided side by side at equal intervals in the lateral direction of the band 10. The presence of the fixing region 40W allows a surface 40A (see FIG. 14) of the auxiliary member 40 on the outer cloth 11 side and the outer cloth 11 to be fixed to each other.

When blood pressure is measured, from the state illustrated in FIG. 12, the second hook-and-loop fastener 8 is pressed against the first hook-and-loop fastener 5 to fix the blood pressure cuff 1 to the upper arm part M. By supplying and discharging air to and from the air bag 7, the compression pressure of the upper arm part M is increased (pressure application) or decreased (pressure reduction). During the pressure application and reduction, the region of the outer cloth 11 overlapping with the auxiliary member 40 in the terminal region Ee and the inner cloth 12 rub against each other. Since the fixing region 40W is present, it is possible to prevent occurrence of stick-slip between the surface 40A of the auxiliary member 40 and the outer cloth 11, which is caused by friction between the outer cloth 11 and the inner cloth 12 in the terminal region Ee. By preventing the occurrence of stick-slip, it is possible to suppress noise at the time of blood pressure measurement and improve the accuracy of blood pressure measurement.

Although five fixing regions 40W are provided in the example of FIG. 13, at least one fixing region may be provided. When only one fixing region 40W is provided, the fixing region 40W is preferably provided in the vicinity of the center in the lateral direction of the auxiliary member 40. In addition, the fixing region 40W is provided like a spot on the auxiliary member 40, but is not limited thereto. For example, the entire surface 40A of the auxiliary member 40 may be fixed to the outer cloth 11, or a linear fixing region extending in the longitudinal direction may be provided on a part of the surface 40A of the auxiliary member 40. The configuration of FIG. 13 has an advantage that the fixing region 40W can be easily formed. Further, the surface of the auxiliary member 40 opposite to the surface 40A (the surface facing the inner cloth 12) may be further fixed to the inner cloth 12. Thus, noise can be further suppressed. Alternatively, the surface of the auxiliary member 40 opposite to the surface 40A (the surface facing the inner cloth 12) is fixed to the inner cloth 12, and the surface 40A of the auxiliary member 40 are not be fixed to the outer cloth 11. Even with this configuration, a noise reduction effect can be expected by suppressing the stick-slip between the inner cloth 12 and the auxiliary member 40.

In addition, instead of providing the fixing region 40W, processing may be performed so that the surface of the outer cloth 11 in the terminal region Ee and the surface of the inner cloth 12 that may come into contact with the surface of the outer cloth 11 easily slide on each other. This can also suppress transmission of a force caused by the outer cloth 11 and the inner cloth 12 rubbing against each other to the auxiliary member 40 and prevent occurrence of stick-slip.

As the thickness of the auxiliary member 40 increases, the noise caused by the stick-slip tends to increase. Therefore, from the viewpoint of suppressing the stick-slip, it is preferable to reduce the thickness of the auxiliary member 40. However, it should be noted that the stick-slip is difficult to completely suppress even when the auxiliary member 40 is made thin.

The auxiliary member 40 described above has, for example, a rectangular plate shape. It is preferable that an angular portion of the rectangular plate shape have a rounded shape (chamfered shape). Since the angular portion of the auxiliary member 40 is rounded, it is possible to reduce pain when the angular portion of the auxiliary member 40 comes into contact with a target measurement site. In addition, it is possible to prevent the angular portion of the auxiliary member 40 from damaging the outer cloth 11 and the inner cloth 12.

While various embodiments have been described with reference to the drawings, needless to say, the present invention is not limited to such examples. It will be apparent to those skilled in the art that various changes and modifications can be made within the scope of the claims, and it is understood that these are naturally belong within the technical scope of the present invention. Further, components of the above-described embodiments may be combined as desired within a range that does not depart from the spirit of the present invention.

REFERENCE NUMERALS LIST

1 Blood pressure cuff
5 First hook-and-loop fastener
5*c* Fastener rear surface member
5*e* Edge side portion
5*k* Raised surface (fastener surface)
8*k* Hook surface (fastener surface)
7 Air bag
7*b* Tube connecting portion
8 Second hook-and-loop fastener
10 Band
11 Outer cloth (first skin member)
11*u*, 12*u* First member
11*i*, 12*i* Second member
12 Inner cloth (second skin member)
15 First opening portion
15*e* Opening edge portion
18 Second opening portion
20 Ring-like member
40 Auxiliary member
Ce Adjacent region
Ee Terminal region
it End edge
ut End edge
Ts Gap
Wp Welded region (first welded region)
Wps Welded region (second welded region)
Wpf1 Welded region (third welded region)
Wpf2 Welded region

The invention claimed is:

1. A blood pressure cuff comprising:
a band enveloping a fluid bag between a first skin member and a second skin member facing the first skin member;
a ring-like member held at a position adjacent to one end edge in a longitudinal direction of the band and extending in a lateral direction of the band; and
an auxiliary member stored inside a terminal region between the one end edge in the longitudinal direction of the band and the ring-like member and extending in the lateral direction, wherein
the ring-like member and the auxiliary member are attached in a state where the ring-like member and the auxiliary member are sandwiched between the first skin member and the second skin member,
the first skin member and the second skin member are welded or bonded to each other in an adjacent region adjacent to the ring-like member and located on a side opposite to the terminal region with the ring-like member sandwiched between the adjacent region and the terminal region, and in an entire region of the terminal region excluding the auxiliary member,
the ring-like member is attached in a state where the ring-like member is sandwiched between the first skin member and the second skin member that are welded or bonded in the adjacent region and the terminal region between the auxiliary member and the ring-like member, and
the auxiliary member is attached in a state where the auxiliary member is sandwiched between the first skin member and the second skin member in the terminal region, the first skin member and the second skin member being welded or bonded in a state of surrounding the auxiliary member entirely, such that rigidity of the terminal region is configured to prevent the terminal region from passing through the ring-like member.

2. The blood pressure cuff according to claim 1, wherein a width of the terminal region in the longitudinal direction is larger than a width of a gap between the band and the ring-like member located outside the band.

3. The blood pressure cuff according to claim 1, wherein a surface of the first skin member on a side of the auxiliary member in the terminal region and the auxiliary member are fixed to each other.

4. The blood pressure cuff according to claim 3, wherein
the first skin member is a member on a side to be not in contact with a target measurement site in a state where the band is wound around and fixed to the target measurement site, and
the second skin member is a member on a side to be in contact with the target measurement site in the state.

* * * * *